(12) United States Patent
Berdugo-Adler et al.

(10) Patent No.: US 11,694,780 B2
(45) Date of Patent: Jul. 4, 2023

(54) SYSTEM AND METHOD FOR ASSIGNING A CANNABIDIOL POINT VALUE AND RECOMMENDING CANNABIDIOL-INFUSED EDIBLES BASED ON BIOLOGICAL PARAMETERS AND ACTIVITY INFORMATION

(71) Applicants: Joelle Berdugo-Adler, Venice, CA (US); Jose R. Rosas Bustos, Santiago (CL)

(72) Inventors: Joelle Berdugo-Adler, Venice, CA (US); Jose R. Rosas Bustos, Santiago (CL)

(*) Notice: Subject to any disclaimer, the term of this patent is extended or adjusted under 35 U.S.C. 154(b) by 475 days.

(21) Appl. No.: 16/432,846

(22) Filed: Jun. 5, 2019

(65) Prior Publication Data
US 2019/0371445 A1    Dec. 5, 2019

Related U.S. Application Data

(60) Provisional application No. 62/820,848, filed on Mar. 19, 2019, provisional application No. 62/680,943, filed on Jun. 5, 2018.

(51) Int. Cl.
| | |
|---|---|
| *A61K 9/00* | (2006.01) |
| *G16H 20/10* | (2018.01) |
| *A61K 31/05* | (2006.01) |
| *G06Q 20/12* | (2012.01) |
| *A61B 5/11* | (2006.01) |

(52) U.S. Cl.
CPC ........... *G16H 20/10* (2018.01); *A61K 9/0056* (2013.01); *A61K 31/05* (2013.01); *G06Q 20/12* (2013.01); *A61B 5/1118* (2013.01)

(58) Field of Classification Search
CPC ................................ G16H 20/10; A61K 31/05
See application file for complete search history.

(56) References Cited

U.S. PATENT DOCUMENTS

| | | | | |
|---|---|---|---|---|
| 2015/0287122 | A1* | 10/2015 | Mak | G06F 3/04883 |
| | | | | 705/26.7 |
| 2017/0259050 | A1* | 9/2017 | Altschul | A61P 25/30 |
| 2020/0135321 | A1* | 4/2020 | Lebrun | G06F 21/33 |
| 2020/0372993 | A1* | 11/2020 | Chu | G16H 20/13 |

* cited by examiner

*Primary Examiner* — Reginald R Reyes
(74) *Attorney, Agent, or Firm* — Polsinelli PC

(57) ABSTRACT

A system and method for assigning a cannabidiol point value and recommending cannabidiol-infused edibles based on biological parameters and activity information. The system and method assign a cannabidiol point value to a cannabidiol-infused edible, and then recommends and delivers a cannabidiol diet to a user based on the user's biological parameters and activity information. An algorithm converts the biological parameters and activity information of the user into a biological and activity point value. At least one cannabidiol-infused edible is assigned a cannabidiol point value. The user scans the cannabidiol-infused edible to ascertain cannabidiol point value. The algorithm derives a recommended cannabidiol dosage for the user based on the association of the cannabidiol point value with the biological and activity point value. The user monitors the cannabidiol point value and consumed cannabidiol-infused edibles on a portable communication device. The cannabidiol-infused edibles are delivered to the user. A licensing fee is charged.

11 Claims, 3 Drawing Sheets

SYSTEM AND METHOD FOR ASSIGNING A CANNABIDIOL POINT VALUE AND RECOMMENDING CANNABIDIOL-INFUSED EDIBLES BASED ON BIOLOGICAL PARAMETERS AND ACTIVITY INFORMATION

CROSS REFERENCE OF RELATED APPLICATIONS

This application claims the benefit of and priority to U.S. Provisional Application No. 62/680,943, filed Jun. 5, 2018, and U.S. Provisional Application No. 62/820,848, filed Mar. 19, 2019, wherein said provisional applications are incorporated herein by reference in their entirety.

FIELD OF THE INVENTION

The present invention relates generally to a system and method for assigning a cannabidiol point value and recommending cannabidiol-infused edibles based on biological parameters and activity information, and, more particularly, relates to a system and method that assigns a biological and activity point value for a user, and a cannabidiol point value to a cannabidiol-infused edible, and then deriving a recommended cannabidiol dosage for the user based on the association of point values; and further, enabling the user to scan and instantly ascertain the cannabidiol content in the edibles; have the edibles delivered to the user; and charge a licensing fee to generate revenue. The system and method is also operable with a supplement-infused edible that is assigned a supplement point value to be associated with the biological parameters and activity information.

BACKGROUND OF THE INVENTION

Generally, cannabidiol is one of at least 113 cannabinoids identified in cannabis. Cannabidiol is a major phytocannabinoid, accounting for up to 40% of the plant's extract. Cannabidiol does not have intoxicating effects like those caused by tetrahydrocannabinol, and may have a downregulating effect on disordered thinking and anxiety. Cannabidiol has been studied scientifically and has the results which show it having many positive attributes, including but not limited to—possible reduction of cancer growth, alleviation of aches and pain, alleviation of depression, repairing of muscles for athletes. It is known in the art that the body has natural cannabinoids that benefit greatly from taking in cannabidiol.

Therefore, a need exists to overcome the problems with the prior art as discussed above.

SUMMARY OF THE INVENTION

The invention provides a system and method for assigning a cannabidiol point value and recommending cannabidiol-infused edibles based on biological parameters and activity information that overcomes the hereinafore-mentioned disadvantages of the heretofore-known devices and methods of this general type and that analyzes at least one user for biological parameters and activity level to assign an appropriate level of cannabidiol infused food and drinks.

With the foregoing and other objects in view, there is provided, in accordance with the invention, a non-transitory program storage device readable by a machine tangibly embodying a program of instructions executable by the machine to perform a method for assigning a cannabidiol point value and recommending cannabidiol-infused edibles based on biological parameters and activity information, the method including collecting a biological parameter and activity information from at least one user, storing the collected biological parameters and activity information in a data storage device, converting, with an algorithm, the biological parameters and activity information into a biological and activity point value, assigning a cannabidiol point value to at least one cannabidiol-infused edible, the cannabidiol point value comprising points equating to a serving size of the cannabidiol-infused edible, monitoring the cannabidiol point value for the cannabidiol-infused edible on a portable communication device, scanning a UPC label or priority bar code associated with the cannabidiol-infused edible to ascertain the assigned cannabidiol point value, associating, with the algorithm, the cannabidiol point value with the biological and activity point value, deriving, by the algorithm, a recommended cannabidiol dosage for the user based on the association of the cannabidiol point value with the biological and activity point value, delivering, with a delivery vehicle, the cannabidiol-infused edible with the recommended cannabidiol dosage to the user, monitoring the cannabidiol consumption on the portable communication device, receiving feedback on the consumption of cannabidiol, and the biological parameters and activity information, and charging a licensing fee for both the delivery and the point values based on use and minimums. The system and method is also operable with a supplement-infused edible that is assigned a supplement point value to be associated with the biological parameters and activity information.

In accordance with a further feature of the present invention, the biological parameters include at least one of the following: weight, height, body mass, and health conditions.

In accordance with a further feature of the present invention, the activity information includes at least one of the following: distance run, weight lifting performance, calories burned, and aerobic activity.

In accordance with a further feature of the present invention, the data storage device includes at least one of the following: a database, a server, and a cloud.

In accordance with a further feature of the present invention, the algorithm derives the recommended cannabidiol dosage with at least one of the following calculation means: range analysis, sorting an array of randomized values, deriving averages from multiple values, deriving means from multiple values, computing the greatest common divisor to two values, and logical deduction.

One objective of the present invention is to provide an appropriate dosage of cannabidiol to the user based on the user's biological parameters and activity information.

Another objective is to generate a point values for cannabidiol content in different edibles.

Another objective is to provide a standardized UPC code for cannabidiol content of edibles.

Another objective is to enable the user to scan the UPC code associated with the cannabidiol-infused edible, to instantly ascertain the cannabidiol content.

Another objective is to enable the user to monitor the cannabidiol point value and cannabidiol consumption on an App directly from a smart phone or watch.

Another objective is to create an API app that allows the user to scan a QR code, RFID code, or any other scannable system code on the cannabidiol-infused edible and keep the tally of cannabidiol dosages on smart watches and phones.

Another objective is to deliver, with a delivery vehicle, the cannabidiol-infused edible with the recommended cannabidiol dosage to the user.

Another objective is to charge a licensing fee for both the delivery and the point values of the biologicals and edibles based on use and minimums.

Another objective is to charge a licensing fee for access to the system and method.

Although the invention is illustrated and described herein as embodied in a System and Method for Assigning a Cannabidiol Point Value and Recommending Cannabidiol-Infused Edibles Based on Biological Parameters and Activity Information, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Before the present invention is disclosed and described, it is to be understood that the terminology used herein is for the purpose of describing particular embodiments only and is not intended to be limiting. The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically. The term "providing" is defined herein in its broadest sense, e.g., bringing/coming into physical existence, making available, and/or supplying to someone or something, in whole or in multiple parts at once or over a period of time.

As used herein, the terms "about" or "approximately" apply to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and explain various principles and advantages all in accordance with the present invention.

DETAILED DESCRIPTION

Figure 1:
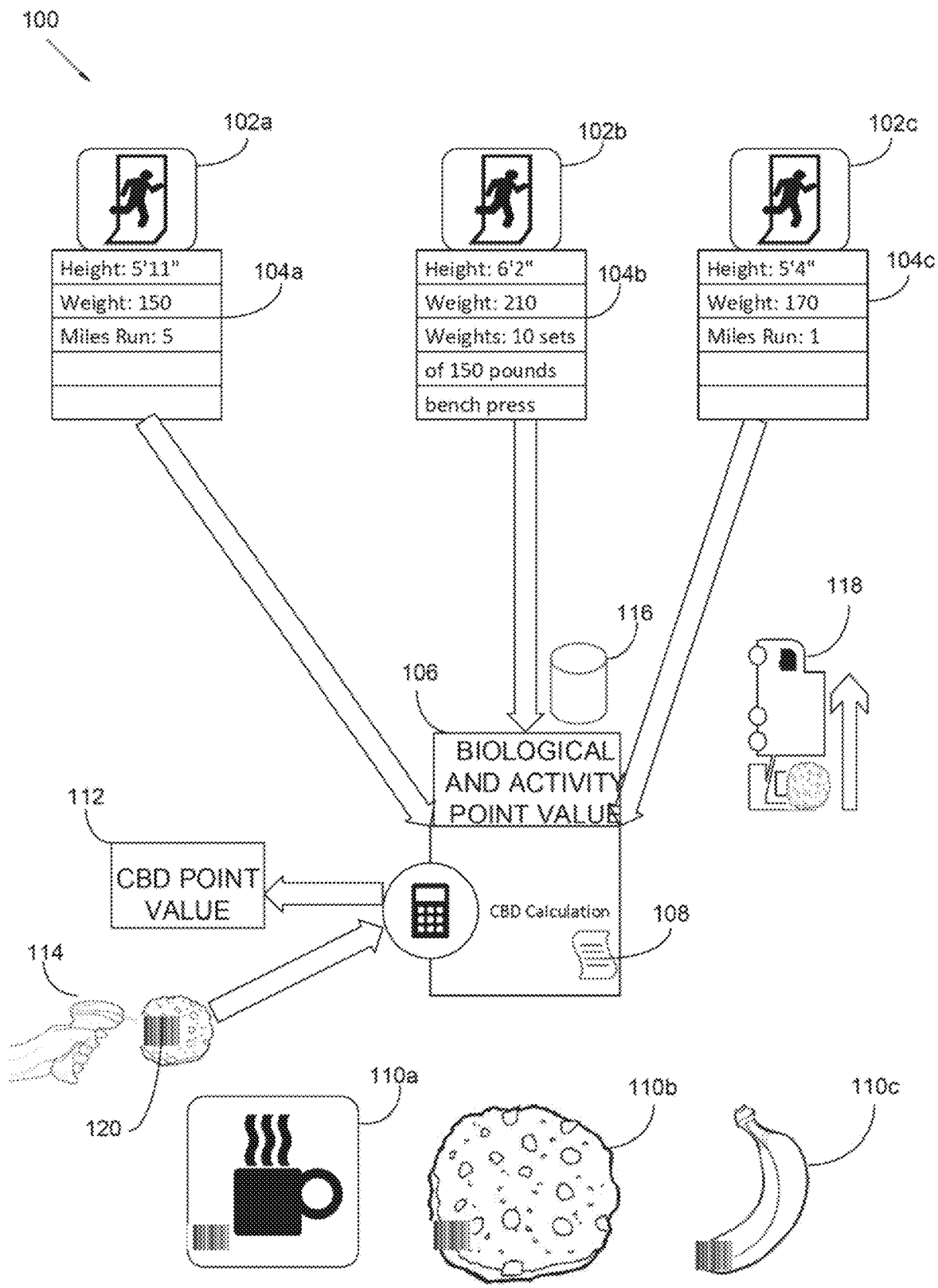
FIG. 1 is a block diagram of an exemplary system for assigning a cannabidiol point value and recommending cannabidiol-infused edibles based on biological parameters and activity information, in accordance with the present invention.

While the specification concludes with claims defining the features of the invention that are regarded as novel, it is believed that the invention will be better understood from a consideration of the following description in conjunction with the drawing figures, in which like reference numerals are carried forward. It is to be understood that the disclosed embodiments are merely exemplary of the invention, which can be embodied in various forms.

The present invention provides a novel and efficient system and method for assigning a cannabidiol point value and recommending cannabidiol-infused edibles based on biological parameters and activity information, hereafter "system 100" and method 200".

As the block diagram in FIG. 1 references, the system 100 assigns a biological and activity point value 106 for at least one user 102a-c. This can be defined as the amount and dosage of cannabis the user can safely consume. The system 100 also assigns a cannabidiol point value 112 to at least one cannabidiol-infused edible 110a-c. This can factor in the type of edible, and the means by which the edible has been infused with cannabis, cannabis extracts, and the like.

After assigning the respective values 106, 112 a recommended cannabidiol dosage for the user 102a-c is derived based on the association of point values 106, 112. For example, an edible with a large dose of cannabis infused would not be appropriate for a user with allow cannabis tolerance or other health concerns. Further, the system 100 is effective in enabling the user 102a-c to scan and instantly ascertain the cannabidiol content in the edibles 110a-c. Once identified, the cannabidiol-infused edible 110a-c may be delivered to the user 102a-c, which can generate revenue. Finally, a licensing fee may be added to generate revenue. The system and method is also operable with a supplement-infused edible that is assigned a supplement point value to be associated with the biological parameters and activity information.

With the foregoing and other objects in view, there is provided, in accordance with the invention, a system 100 for assigning a cannabidiol point value and recommending cannabidiol-infused edible 110a-cs based on biological parameters and activity information 104a-c. The system 100 initially involves at least one user 102a-c interested in consuming a recommended dosage of cannabidiol, based on biological and activity—specific to the user. However, in alternative embodiments, the system 100 may also be used with, for example, consuming appropriate dosages of any type of supplements or substance, including: vitamins, minerals, and nutrients, such as Vitamin D, Iron, and the like that are infused into the edible or other consumable liquid, gel, or solid substance.

The biological parameters and activity information 104a-c of user 102a-c are collected from the user 102a-c through various biological and athletic measuring means known in the art. For example, the weight can be measured with a scale; while the running capacity of the user 102a-c can be measured with a stop watch. The biological parameters and activity information 104a-c are one of the factors in determining the appropriate cannabidiol-infused edible 110a-c for the user 102a-c.

In some embodiments, the biological parameters may include, without limitation, weight, height, body mass, and health conditions of the user 102a-c. The biological parameters may vary accordingly. For example, FIG. 1 illustrates a first user 102a-c having a weight of 150 pounds and a height of 5'11"; and a second user 102a-c having a weight of 210 pounds and a height of 6'2". In other embodiments, the activity information 104a-c may include, without limitation, a distance run, weight lifting performance, calories burned, and aerobic activity.

A data storage device 116 is used to store the biological parameters and activity information 104a-c. The data storage device 116 may also be effective for storing the user 102a-c profile. This archiving aspect of the system 100 helps understand the user and other physical needs better, so as to recommend appropriate dosages of cannabidiol. In some embodiments, the data storage device 116 may include, without limitation, a database, a server, and a cloud.

The system 100 also provides an algorithm 108 that is configured to convert the biological parameters and activity information 104a-c into a biological and activity point value 106. This point value 106 helps quantify the biological and activity characteristics of the user 102a-c, so as to enable appropriate recommendation of cannabidiol dosages, as discussed below.

The algorithm 108 may utilize various functions to derive the biological and activity point value 106, including: range analysis, sorting an array of randomized values, deriving averages from multiple values, deriving means from multiple values, and computing the greatest common divisor to two values, and logical deduction. Other point calculation and averaging means, along with matching algorithms, known in the value processing art may also be used.

As discussed above, a cannabidiol-infused edible 110a-c is used for consuming the cannabidiol. The cannabidiol-infused edible 110a-c may include a food or drink, such as tea, cookies, bananas, protein bars, salad dressing, health shake, tea, etc. The system 100 assigns a cannabidiol point value 112 to the cannabidiol-infused edible 110a-c. The cannabidiol point value 112 includes points that equate to a serving size of the cannabidiol-infused edible 110a-c. For example, a cookie 110a can have 15 mg cannabidiol, while a banana can have 5 mg cannabidiol. Those skilled in the art will recognize that cannabidiol is a phytocannabinoid that has one of some 113 identified cannabinoids in cannabis plants, accounting for up to 40% of the plant's extract. While the present invention is intended for use with Cannabidiol, in other embodiments, the system 100 and method 200 may also be applicable with tetrahydrocannabinol.

Looking again at FIG. 1, a UPC label or priority bar code can be affixed, or at least associated, with the cannabidiol-infused edible 110a-c. In this manner, a standardized cannabidiol content for each edible 110a-c is established. The system 100 allows the user 102a-c to scan a UPC label or priority bar code 120 associated with the cannabidiol-infused edible 110a-c, so as to ascertain the cannabidiol point value 112. A scanner 114 may be used for these scanning purposes. By scanning in such a manner, a standardized dosage of cannabidiol can be ascertained for each type of cannabidiol-infused edible 110a-c. For example, a cookie 110b can have 15 mg cannabidiol; and a banana 110c can have 5 mg of cannabidiol infused therein.

The scanned cannabidiol point value 112 for the cannabidiol-infused edible 110a-c can be monitored on a portable communication device by the user 102a-c. This creates a real time, archived means for the user to ascertain the cannabidiol content of the edibles. This also standardizes the cannabidiol content for edibles. The portable communication device may include, without limitation, a smart phone, a tablet, a watch, a laptop, and a computer.

In one exemplary use, an API app on a smart phone or watch allows the user 102a-c to scan a QR code, RFID code, or any other scannable system code on the cannabidiol-infused edible 110a-c. This allows the user to keep the tally of cannabidiol dosages directly viewable from the smart phone or watch. The scannable system codes may be either visible or hidden; there may be multiple scannable system codes associated with each stock keeping unit (SKU). There may be one SKU, or multiple SKU. Further, the SKU may be hidden. The scannable code is stored in a distributed network which can be private, or on an existing IT infrastructure.

The algorithm 108 then associates the cannabidiol point value 112 with the biological and activity point value 106 derived earlier from the user 102a-c. This association is computed in the algorithm 108 to derive a recommended cannabidiol dosage for display, whether digitally through a graphical user interface (GUI) or printed, to the user 102a-c. The recommended cannabidiol dosage is based, at least partially, on the biological and activity information 104a-c of the user 102a-c, and the cannabidiol point value 112 of the edibles 110a-c.

In one embodiment, the software application displays a chart displaying a recommended dosage based, dictated, or being a function of one or more biological and activity information 104a-c of the user. Charts and/or personal profiles of the user are important for the present invention, so that the user will visit the administrator and see what the dosage is suggested. In other embodiments, the algorithm 108 is configured to derive a recommended cannabidiol dosage for the user 102a-c based on the association of the cannabidiol point value 112 with the biological and activity point value 106.

In this manner, an effective amount of cannabidiol is delivered to the user 102a-c. As discussed above, the algorithm 108 may utilize various functions to derive the a recommended cannabidiol dosage for the user 102a-c, including: range analysis, sorting an array of randomized values, deriving averages from multiple values, deriving means from multiple values, and computing the greatest common divisor to two values, and logical deduction.

For example, based on the recommended cannabidiol dosage, a high performing athlete training every day generates 5 biological and activity value points 106, and requires 10 cannabidiol value points 112, or approximately 1500 mg of cannabidiol throughout the day in doses of 5-15 mg per serving. Therefore, if the athlete consumes a cookie which has 15 mg of cannabidiol, 100 cookies would have to be consumed. However, the athlete could also consume other cannabidiol infused edibles, such as ice cream, protein powder, salad dressing, and protein bars. However, in other embodiments, each serving of the edible 110a-c can be between 1 to 10 points, with the user selecting edibles that match the points.

In some embodiments, the system 100 provides a means to deliver the cannabidiol-infused edibles 110a-c to the user 102a-c. A delivery vehicle 118 may be used to deliver the cannabidiol-infused edible 110a-c with the recommended cannabidiol dosage to the user 102a-c. The user 102a-c may also monitor the cannabidiol consumption on the portable communication device. In this manner, the user, or a coach, is aware of not only the amount of cannabidiol consumed, but also the biological and activity of the user.

Further, the user 102a-c can also receive feedback on the consumption of cannabidiol and biological parameters and activity information 104a-c. The feedback is effective for altering physical and eating habits of the user 102a-c. For example, the user 102a-c can increase distances run, and cannabidiol consumption simultaneously. In some embodiments, a licensing fee may be charged for both the delivery and the point values based on use and minimums. For example, every scan by the user 102a-c is charged. And every delivery of cannabidiol-infused edible 110a-c having the recommended cannabidiol dosage.

Furthermore, the system 100 provides a unique counterfeit-prevention feature. This includes real time inventory of edibles, and an SKU that is anti-counterfeit. Also, the system 100 provides a high level analytic of consumer buying and using stats. Also, the geolocation of the edibles is monitored by a positioning system, so as to reduce counterfeiting the bar codes or edibles. The geolocation is uploaded and viewable on a smart phone for easy access and analysis.

Information is a two-way communication info uploaded and downloaded consumers build data for company's analytics and oversight of potential counterfeiting or personal experience on product. This may include, without limitation, surveys, rating, registration of product, referral potential, and general use ideas and stats. The software application also facilitates consumers and users to describe the product manually or add any pertinent data describing the geolocation. This enhances authenticity by becoming part of the library of stats and benchmarks, which continually add to the stored data.

Figure 2:
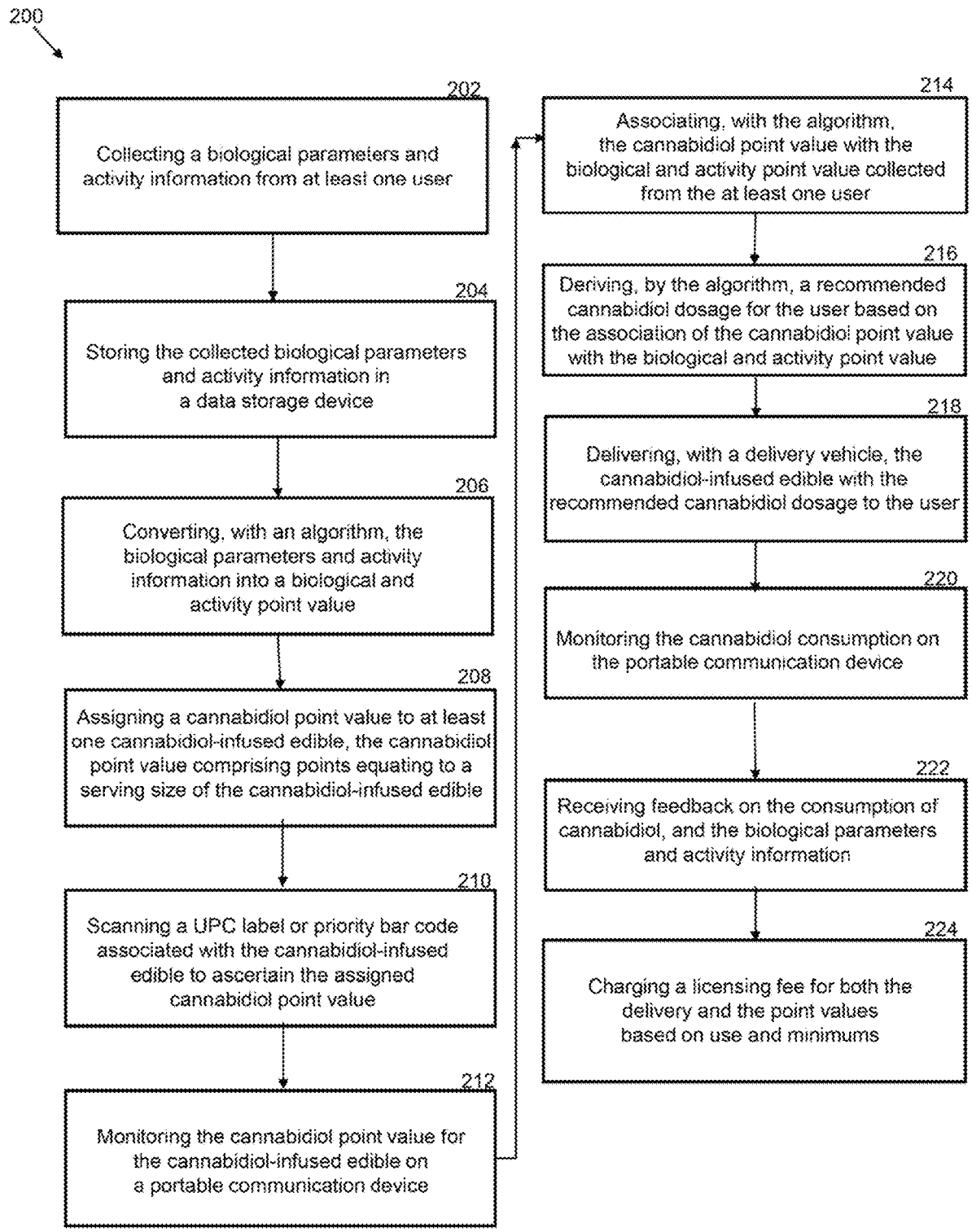
FIG. 2 is a flowchart diagram of an exemplary method for assigning a cannabidiol point value and recommending cannabidiol-infused edibles based on biological parameters and activity information, in accordance with the present invention.

FIG. 2 illustrates a flowchart diagram of an exemplary method 200 for assigning a cannabidiol point value and recommending cannabidiol-infused edibles based on biological parameters and activity information. The method 200 may include an initial Step 202 of collecting a biological parameters and activity information from at least one user. The method 200 may further comprise a Step 204 of storing the collected biological parameters and activity information in a data storage device. A Step 206 includes converting, with an algorithm, the biological parameters and activity information into a biological and activity point value.

In some embodiments, a Step 208 comprises assigning a cannabidiol point value to at least one cannabidiol-infused edible, the cannabidiol point value comprising points equating to a serving size of the cannabidiol-infused edible. A Step 210 includes scanning a UPC label or priority bar code associated with the cannabidiol-infused edible to ascertain the cannabidiol point value. In some embodiments, a Step 212 may include monitoring the cannabidiol point value for the assigned cannabidiol-infused edible on a portable communication device. In alternative embodiments, a Step includes assigning a supplement point value to at least one supplement-infused edible, the supplement point value comprising points equating to a serving size of the supplement-infused edible A Step 214 comprises associating, with the algorithm, the cannabidiol point value with the biological and activity point value collected from the at least one user. An alternative embodiment includes associating, with the algorithm, the supplement point value with the biological and activity point value collected from the user. A Step 216 includes deriving, by the algorithm, a recommended cannabidiol dosage for the user based on the association of the cannabidiol point value with the biological and activity point value. In one alternative embodiment, a Step includes deriving, by the algorithm, a recommended supplement dosage for the user based on the association of the supplement point value with the biological and activity point value. The method 200 further comprises a Step 218 of delivering, with a delivery vehicle, the cannabidiol-infused edible with the recommended cannabidiol dosage to the user.

In some embodiments, a Step 220 may include monitoring the cannabidiol consumption on the portable communication device. An alternative Step includes a Step 220 may include monitoring the supplement consumption on the portable communication device. The method 200 further comprises a Step 222 comprises receiving feedback on the consumption of cannabidiol, and the biological parameters and activity information. A final Step 224 comprises charging a licensing fee for both the delivery and the point values based on use and minimums. The licensing fee includes an amount of money paid by an individual or business to a government agency for the privilege of engaging in the method 200. Fees apply to the plan that can be for one user, or multiple users. Further, a software application of the method may be acquired by companies as a white label, where each company has a version of the software application.

Although the process-flow diagrams show a specific order of executing the process steps, the order of executing the steps may be changed relative to the order shown in certain embodiments. Also, two or more blocks shown in succession may be executed concurrently or with partial concurrence in some embodiments. Certain steps may also be omitted from the process-flow diagrams for the sake of brevity. In some embodiments, some or all the process steps shown in the process-flow diagrams can be combined into a single process.

These and other advantages of the invention will be further understood and appreciated by those skilled in the art by reference to the following written specification, claims and appended drawings.

Because many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalence.

Figure 3:
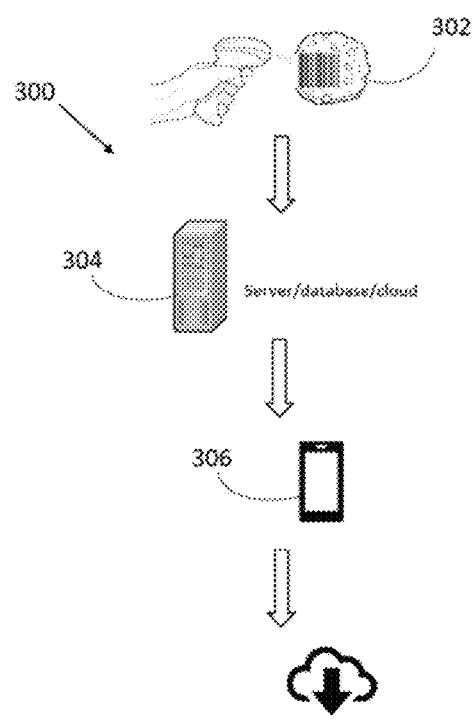
FIG. 3 is a process chart showing the cannabidiol-infused edibles being scanned, and the cannabidiol point value being stored for analysis of the user's biological parameters and activity information, in accordance with the present invention.

FIG. 3 illustrates another block diagram of an exemplary system and method for identifying and detecting counterfeit cannabidiol-infused edible products. A first step may include scanning a UPC label or priority bar code associated with a cannabidiol-infused edible 302. A next step may include uploading the product information garnered in the previous step of scanning the UPC label to a local database 304 server or cloud-based database over a network, e.g., the Internet. Such product information may include, without limitation, the product's UPC label or priority bar code, the product's geo-location, statistics of users' purchase and consumption histories, and any and all information provided by the manufacturer. The geo-location, or estimation of the real-world geographic location of an object, may be determined using the scanning device that is operably coupled to the Internet or using satellite communications. In its simplest form geolocation, involves the generation of a set of geographic coordinates and is closely related to the use of positioning systems, but its usefulness is enhanced using these coordinates to determine a meaningful location, such as a street address. Said another way, geolocation may also refer to the latitude and longitude coordinates of a particular location to identify where a product is located. The term and definition have been standardized by real-time locating system standard ISO/IEC 19762-5:2008.

Next, the aforementioned product information becomes part of a library of statistics and benchmarks, which may be displayed in the software application on a mobile device 306 of a user or accessible by a product manufacture, producer, or distributor. Product information is continuously updated for each scan. As such, said manufacturer(s) may access and use product information to detect the sale or distribution of any counterfeit cannabidiol-infused edibles. Furthermore, said process can also be utilized by product manufacture(s) to ascertain whether or not a scanned product is a counterfeit. Therefore, information may be exchanged through a two-way communication configuration with information uploaded and downloaded by consumers to build one or more database(s) for third-party analytics and oversight of potential counterfeiting or personal experience on product which can include surveys, rating, registration of product, referral potential and general use ideas or statistics. A next step may include converting, with an algorithm, the product information into a prediction of the probability that the cannabidiol-infused edible product is counterfeit.

What is claimed is:

1. A non-transitory program storage device readable by a machine tangibly embodying a program of instructions executable by the machine to perform a method, the method comprising:
    assigning a cannabidiol point value to at least one cannabidiol-infused edible, the cannabidiol point value corresponding to a serving size of cannabidiol in the cannabidiol-infused edible;
    affixing, to an aspect of the at least one cannabidiol-infused edible, a UPC label or priority bar code comprising a scannable image of the assigned cannabidiol point value;
    collecting, by the machine and from a wearable computing device of at least one user, a biological parameter and activity information of the at least one user;
    storing, in a data storage device, the collected biological parameters and activity information;
    converting the biological parameters and activity information into a biological and activity point value quantifying at least one biological characteristic of the at least one user;
    deriving a recommended cannabidiol dosage of consuming the at least one cannabidiol-infused edible for the at least one user based on an association of the cannabidiol point value of the at least one cannabidiol-infused edible with the biological and activity point value of the at least one user;
    receiving, from a scanner, the assigned cannabidiol point value obtained from the UPC label or priority bar code proximate to the at least one cannabidiol-infused edible;
    transmitting, to the scanner, the recommended cannabidiol dosage of consuming the at least one cannabidiol-infused edible for the at least one user;
    receiving, by the machine, a geolocation of the at least one cannabidiol-infused edible;
    monitoring the geolocation of the at least one cannabidiol-infused edible to prevent counterfeiting of the at least one cannabidiol-infused edible;
    delivering, with a delivery vehicle and based on the recommended cannabidiol dosage and the geolocation of the at least one cannabidiol-infused edible, the cannabidiol-infused edible to the at least one user; and
    receiving feedback on the consumption of cannabidiol and the biological parameters and activity information.

2. The method according to claim 1, further comprising: monitoring the cannabidiol point value for the at least one cannabidiol-infused edible on a portable communication device.

3. The method according to claim 1, further comprising:
    receiving, from a portable communication device, an indication of a consumption of the at least one cannabidiol-infused edible; and
    tracking, on the portable communication device, the consumption of the at least one cannabidiol-infused edible.

4. The method according to claim 1, wherein:
    the biological parameter includes at least one of the following: a weight of the at least one user, a height of the at least one user, a body mass of the at least one user, and a health condition of the at least one user.

5. The method according to claim 1, wherein:
    the activity information includes at least one of the following: a distance run by the at least one user, a weight lifting performance of the at least one user, an amount of calories burned by the at least one user, and an aerobic activity of the at least one user.

6. The method according to claim 1, wherein:
    the data storage device includes at least one of the following: a database, a server, and a cloud.

7. The method according to claim 1, wherein
    deriving the recommended cannabidiol dosage comprises determining at least one of the following: a range analysis, sorting an array of randomized values, deriving averages from multiple values, deriving means from multiple values, computing the greatest common divisor to two values, and logical deduction.

8. The method according to claim 1, further comprising: charging a licensing fee for delivering the cannabidiol-infused edible to the at least one user, assigning the cannabidiol point value to the at least one cannabidiol-infused edible, and deriving a recommended cannabidiol dosage of consuming the at least one cannabidiol-infused edible for the at least one user.

9. The method according to claim 8, wherein the licensing fee is based at least on a consumption of the at least one cannabidiol-infused edible and a minimum fee value.

10. The method of claim 2 wherein the portable communication device comprises the scanner.

11. The method of claim 1 wherein the geolocation is one of a set of geographic coordinates, a latitude and longitude coordinates, or a street address.

* * * * *